United States Patent
Moon et al.

(10) Patent No.: US 9,848,962 B2
(45) Date of Patent: Dec. 26, 2017

(54) DRILL FOR IMPLANT SURGERY

(75) Inventors: Jong Hoon Moon, Busan (KR); Tae Gwan Eom, Busan (KR); Tae Euk Lee, Busan (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 245 days.

(21) Appl. No.: 13/522,004

(22) PCT Filed: Sep. 13, 2010

(86) PCT No.: PCT/KR2010/006201
§ 371 (c)(1),
(2), (4) Date: Aug. 30, 2012

(87) PCT Pub. No.: WO2011/087200
PCT Pub. Date: Jul. 21, 2011

(65) Prior Publication Data
US 2012/0323243 A1  Dec. 20, 2012

(30) Foreign Application Priority Data
Jan. 14, 2010 (KR) ........................ 10-2010-0003589

(51) Int. Cl.
*A61C 8/00* (2006.01)
*A61B 17/16* (2006.01)

(52) U.S. Cl.
CPC ........ *A61C 8/0089* (2013.01); *A61B 17/1615* (2013.01); *A61B 17/1688* (2013.01); *A61C 8/0092* (2013.01)

(58) Field of Classification Search
CPC ............ A61B 17/1615; A61B 17/1637; A61B 17/1688; A61B 17/1695; B23B 2251/18;
(Continued)

(56) References Cited

U.S. PATENT DOCUMENTS 693,508 A * 2/1902 Fette .......................... B23C 5/10
144/240
3,452,625 A * 7/1969 Russo ..................... B23B 51/02
408/223
(Continued)

FOREIGN PATENT DOCUMENTS

JP         8-229720 A     9/1996
JP      2009-131634 A     6/2009
(Continued)

OTHER PUBLICATIONS

International Search Report dated Jun. 29, 2011, for PCT/KR2010/006201, 3 pages.

*Primary Examiner* — Matthew Lawson
*Assistant Examiner* — Amy Sipp
(74) *Attorney, Agent, or Firm* — Seed IP Law Group LLP

(57) ABSTRACT

A drill for an implant surgery is provided which allows a mucous membrane in the maxillary sinus to be quickly and safely lifted without being damaged during a surgery for the maxillary sinus. The drill for use in an implant surgery includes a connection portion formed at an upper end of a body of the drill to be connected with a driving device; and a cutting portion formed at a lower end of the body and having a cutting blade for drilling, wherein an outer circumferential edge of a distal end of the cutting portion protrudes rather than a center of the distal end of the cutting portion.

5 Claims, 2 Drawing Sheets

(58) Field of Classification Search
CPC ..... B23B 51/02; B23B 2251/04; B23B 51/00; B23B 2251/082; B23B 2251/426; B23C 5/12; B23C 5/14; B23C 2210/084; A61C 3/02; A61C 8/0089
USPC ..... 606/80, 84, 180; 433/165, 166; 408/223, 408/224, 227–230, 211; 407/34, 42, 53, 407/54, 61–63
See application file for complete search history.

(56) References Cited

U.S. PATENT DOCUMENTS

| | | | | |
|---|---|---|---|---|
| 5,514,141 | A * | 5/1996 | Prizzi, Jr. | A61B 17/1637 606/180 |
| 5,941,706 | A * | 8/1999 | Ura | A61B 17/16 433/165 |
| 5,964,555 | A * | 10/1999 | Strand | B23B 31/1107 279/93 |
| 6,846,135 | B2 * | 1/2005 | Kuroda | B23C 5/10 407/34 |
| 6,976,815 | B2 * | 12/2005 | Berglow | B23C 5/10 407/54 |
| 7,402,004 | B2 * | 7/2008 | Tanaka | B23C 5/10 407/53 |
| 7,753,624 | B2 * | 7/2010 | Gunther | B23C 5/10 407/30 |
| 7,927,046 | B2 * | 4/2011 | Tanaka | B23C 5/10 407/53 |
| 7,997,834 | B2 * | 8/2011 | Aoki | B23C 5/10 407/113 |
| 8,591,232 | B2 * | 11/2013 | Heo | A61C 3/02 433/165 |
| 2003/0180104 | A1 * | 9/2003 | Kuroda | B23C 5/10 407/54 |
| 2006/0060053 | A1 * | 3/2006 | Tanaka | B23C 5/10 83/663 |
| 2007/0258777 | A1 * | 11/2007 | Gunther | B23C 5/10 407/83 |
| 2008/0286056 | A1 * | 11/2008 | Tanaka | B23C 5/10 407/53 |
| 2009/0060663 | A1 * | 3/2009 | Rouge | B23C 5/10 407/44 |
| 2009/0142731 | A1 | 6/2009 | Kim | |
| 2010/0143052 | A1 * | 6/2010 | Aoki | B23C 5/10 407/54 |
| 2010/0196844 | A1 * | 8/2010 | Heo | A61C 3/02 433/114 |

FOREIGN PATENT DOCUMENTS

| | | |
|---|---|---|
| KR | 20-0338095 Y1 | 1/2004 |
| KR | 10-0792649 B1 | 1/2008 |
| KR | 10-0838942 B1 | 6/2008 |
| KR | 10-2009-0056395 A | 6/2009 |
| WO | 2009/008606 A2 | 1/2009 |
| WO | 2009/099267 A1 | 8/2009 |

* cited by examiner

[Fig. 1]
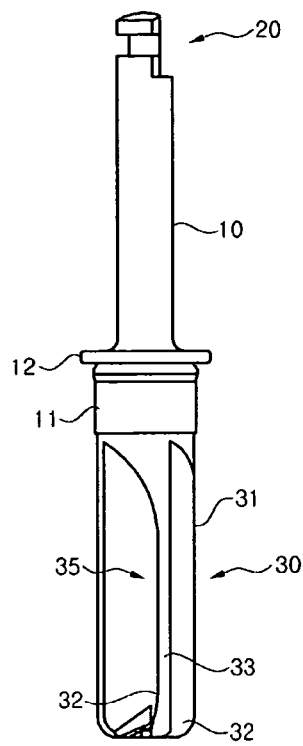
[Fig. 2]
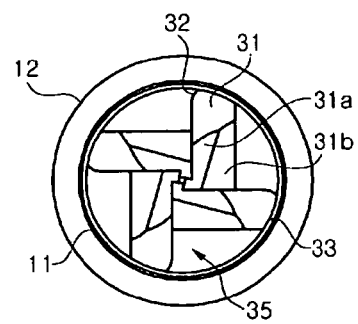
[Fig. 3]
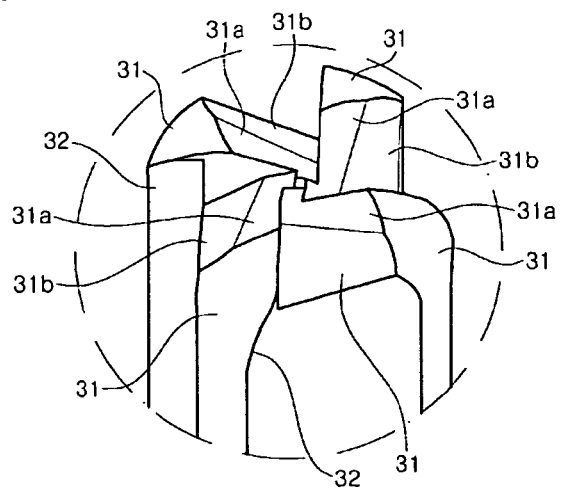

[Fig. 4]
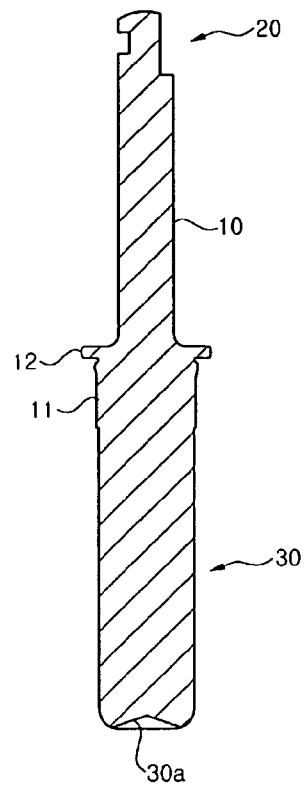
[Fig. 5]
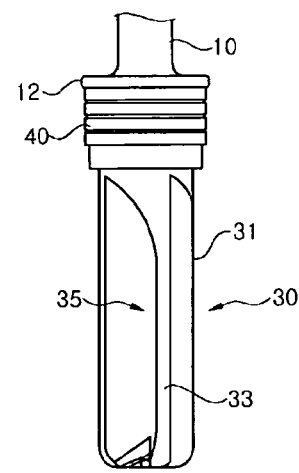
[Fig. 6]
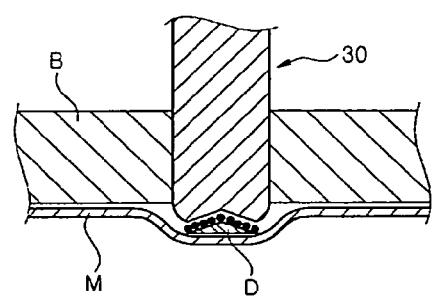

DRILL FOR IMPLANT SURGERY

BACKGROUND

Technical Field

The present disclosure relates to a drill used for an implant surgery for recovering a lost tooth of a patient, and more particularly, to a drill for an implant surgery which allows a mucous membrane in the maxillary sinus to be fast and safely lifted without being damaged during a surgery for the maxillary sinus.

Description of the Related Art

A conventional implant surgery method for the maxillary sinus has been classified into two kinds of approaches, i.e., a lateral approach and a crestal approach.

In the conventional crestal approach, an osteotome surgery using an osteotome surgery kit has been widely used. In the osteotome surgery, drilling processes are executed from an initial drilling stage to a final drilling stage according to an implant surgery plan, and then a malleting process is conducted by using the osteotome surgery kit. At this time, the cortical bone is lifted and at the same time its surrounding cancellous bone is compressed, so that a denture may be implanted. However, during this surgery, the malleting process induces impacts and noise, so that a patient may feel a pain such as a headache, and thus an operator has no choice but to execute a surgical procedure under the psychologically unstable state due to any possible pain of the patient.

The cranial bone of a human body has empty spaces such as maxillary sinuses, frontal sinuses and sphenoidal sinuses, which serve to reduce the weight of the cranial bone and cause a sound to be resonated, and there are mucous membranes between such empty spaces and the cranial bone. The existence of such mucous membranes disturbs the implant surgery when an operator tries to approach the maxillary sinus and implant a denture.

Problems at the surgery may occur when the maxillary sinus is drilled for the purpose of implanting a denture in the empty space of the maxillary sinus. In other words, the mucous membrane in the maxillary sinus may be easily torn when a blade of a drill for use in an implant surgery comes in contact with the mucous membrane during the rotation of the drill for the perforation of the maxillary sinus or an operator applies an excessive force instantly and inadvertently. The torn mucous membrane may cause problems such as infection, so that an operator should be always cautious in order not to tear the mucous membrane.

While performing a drilling work by rotating the drill, the operator mostly determines the perforation of the maxillary sinus depending on his/her feeling at fingertips. The operator generally checks a perforation depth by measuring the thickness of the maxillary sinus with X-ray or computerized tomography (CT) before performing the surgery. However, since the bone in the maxillary sinus has various shapes such as planar shape, concave shape and septum shape so that the mucous membrane may be perforated due to various inner shapes of the maxillary sinuses, the operator always feels psychologically burdened during the surgery.

In order to lessen the burden of the operator as described above, various methods have been proposed. For example, a drill tip may be made blunt in order that the mucous membrane cannot be torn even though the rotating drill tip comes into contact with the mucous membrane. Alternatively, a drill may be designed to be rotated at a lower speed or at a manually controlled speed in which a cutting ability of the drill is reduced. In another case, a diamond grit of small particles may be attached to a tool so as to gnaw the bone.

However, since the drilling work is performed at a lower speed to prevent the mucous membrane from being torn in the conventional drills, there is a disadvantage in that the drilling work may take a long time.

In addition, there are other problems in that cut bone chips cannot be easily cut and discharged, some cut portions of the bone during the drilling operation may be abruptly and locally heated due to a frictional heat between the drill and the cut portions, and the mucous membrane may be perforated while the operator inadvertently gives an excessive force thereto.

BRIEF SUMMARY

Embodiments of the present invention solve the aforementioned problems in the prior art. For example, embodiments of the present invention provide a drill capable of preventing a mucous membrane in a maxillary sinus from being damaged by quickly and safely lifting the mucous membrane in the maxillary sinus due to a safety structure at a drill tip of the drill even though the drill comes in direct contact with the mucous membrane in the maxillary sinus while the drill keeps the same inherent functions as the conventional drills, i.e., the perforation or reaming of the cortical bone or the cancellous bone in the crestal approach which is an implant surgery for the maxillary sinus, thereby ensuring safety and convenience in the implant surgery as well as enhancing the clinical success rate after the surgery.

According to an aspect of the present invention, there is provided a drill for use in an implant surgery, which includes a connection portion formed at an upper end of a body of the drill to be connected with a driving device; and a cutting portion formed at a lower end of the body and having a cutting blade for drilling, wherein an outer circumferential edge of a distal end of the cutting portion protrudes rather than a center of the distal end of the cutting portion.

A concave portion with the center concavely depressed is formed at the distal end of the cutting portion, so that a bone disk is formed at the distal end of the cutting portion during a drilling work, thereby preventing a mucous membrane from being damaged.

The outer circumferential edge of the cutting portion is rounded. Accordingly, a mucous membrane can be prevented from being damaged even though the cutting portion is in direct contact with the mucous membrane during a drilling work.

The cutting portion has one or more cutting blades, and each of the cutting blades has one or more sloped surface at an inner side of a tip thereof.

Each cutting blade has a guide of a predetermined thickness at a side surface thereof. Accordingly, the drill can be prevented from being shaken during a drilling work.

The cutting blade includes a leading edge portion curved toward a leading direction as it goes to a distal end of the cutting blade.

A chip pocket is formed between the cutting blades so that cut bone chips are easily discharged therethrough and stored therein.

A stepped portion protruding outwards and a stop portion further protruding outwards from a proximal end of the stepped portion are formed on an outer circumference of the body between the connection portion and the cutting portion, whereby a stopper member for restricting a drilling depth may be fixedly fit around the stepped portion.

According to embodiments of the present invention so constructed, it is possible to provide a drill capable of preventing a mucous membrane in an maxillary sinus from being damaged by quickly and safely lifting the mucous membrane in the maxillary sinus due to a safety structure at a drill tip of the drill even though the drill comes in direct contact with the mucous membrane in the maxillary sinus while the drill keeps the same inherent functions as the conventional drills, i.e., the perforation or reaming of the cortical bone or the cancellous bone in the crestal approach which is an implant surgery for the maxillary sinus.

If the drill for the implant surgery according to embodiments of the present invention is used, the safety structure at the drill tip forms the bone disk at the drill tip. As such, this bone disk prevents the drill blade from being in direct contact with the mucous membrane in the maxillary sinus, so that the mucous membrane in the maxillary sinus can be quickly and safely lifted.

In addition, if the drill for the implant surgery according to embodiments of the present invention is used, the outer circumferential edge of the drill tip is rounded. As such, the mucous membrane in the maxillary sinus can be safely lifted even though the bone disk is not formed and the drill blade is in direct contact with the mucous membrane in the maxillary sinus.

According to embodiments of the present invention so constructed, during the surgery of the maxillary sinus, an operator may approach the mucous membrane in the maxillary sinus faster and then lift the mucous membrane safely, and therefore there are provided many advantages in that the operation area may be smaller, an edema may be restricted after the surgery, and the bone implant to be used may be reduced.

In addition, since the malleting process which otherwise would be used at the conventional surgery, such as the osteotome surgery, is not performed according to embodiments of the present invention, it is possible to lessen the pain of a patient. Further, considering that the mucous membrane in the maxillary sinus is quickly and safely lifted, an operator may perform the surgery with convenience and mental stability against surgery, and the clinical success rate can be enhanced after the successful surgery.

BRIEF DESCRIPTION OF THE SEVERAL VIEWS OF THE DRAWINGS

FIG. 1 is a front view showing a drill for an implant surgery according to one embodiment of the present invention.

FIG. 2 is a plan view showing the drill for the implant surgery of FIG. 1.

FIG. 3 is a perspective view of a main part of the drill for the implant surgery of FIG. 1.

FIG. 4 is a front cross-sectional view showing the drill for the implant surgery of FIG. 1.

FIG. 5 is a partial front view of the drill for the implant surgery of FIG. 1, with a stopper mounted thereto.

FIG. 6 is a conceptual diagram illustrating an operation of the drill for the implant surgery of FIG. 1.

EXPLANATION OF REFERENCE NUMERALS FOR MAJOR PORTIONS SHOWN IN DRAWINGS

| 10: body | 11: stepped portion |
| 12: stop portion | 20: connection portion |

-continued

| 30: cutting portion | 31: cutting blade |
| 31a: first sloped surface | 31b: second sloped surface |
| 32: tip | 33: guide |
| 35: chip pocket | B: bone |
| D: bone disk | M: mucous membrane |

DETAILED DESCRIPTION

Hereinafter, a particularly advantageous embodiment of a drill for an implant surgery according to the present invention will be described in detail with reference to the accompanying drawings.

The drill according to embodiments of the present invention may be used at high and low speeds. If the drill is coupled with a hand driver, the drill may be used in a low-speed mode. If the drill is coupled with a dental surgery engine, the drill may be used in any mode of the high-speed and low-speed modes.

As shown in FIGS. 1 to 4, the drill for the implant surgery according to a particularly advantageous embodiment of the present invention is composed of a body 10 having a generally cylindrical shape. The drill includes a connection portion 20 formed at one end, i.e., an upper end, of the body 10 to be connected with a driving device such as the hand driver and the dental surgery engine as described above, and a cutting portion 30 formed at the other end, i.e., a lower end, of the body 10 and having cutting blades 31 for drilling.

A distal end of the cutting portion 30 has a concave portion 30a (FIG. 4) whose center is concavely depressed to be shaped as a reverse conical shape, so that a bone disk D may be formed at a tip during a drilling work as will be explained later with reference to FIG. 6. Since the bone disk D prevents the cutting blade 31 of the drill from being in direct contact with a mucous membrane M, for example a mucous membrane in the maxillary sinus, the mucous membrane in the maxillary sinus may be safely lifted.

Also, an outer circumferential edge of the cutting portion 30 is rounded. Thus, even though the cutting blade 31 of the drill is in direct contact with the mucous membrane M in the maxillary sinus without forming the bone disk D, the mucous membrane in the maxillary sinus may be safely lifted. In other words, since the inner structure of the maxillary sinus is shaped as irregular shapes, the cutting blade 31 cannot approach the mucous membrane in the maxillary sinus in a direction which is perpendicular to the mucous membrane. However, even if it were so, embodiments of the drill of the present invention, in which the outer circumferential edge of the cutting portion 30 is rounded, may prevent the mucous membrane in the maxillary sinus from being damaged.

The number of cutting blades 31 formed at the cutting portion 30 is preferably two or more so as to improve the cutting performance thereof. FIGS. 2 and 3 exemplarily show that four cutting blades 31 are formed in total.

Each cutting blade 31 may have a plurality of sloped surfaces at an inner side of its tip to improve the cutting ability for drilling. It is preferable that the cutting ability is improved as mentioned above, which is because a cutting speed may be flexibly controlled from a low speed to a high speed. In particular, the low-speed rotation allows bone chips to be collected, while the high-speed rotation allows a surgery time to be shortened, so that an operator may perform a surgical operation with convenience for surgery.

FIGS. 2 and 3 exemplarily show that each cutting blade 31 has two sloped surfaces, namely a first sloped surface 31*a* and a second sloped surface 31*b*.

The number of cutting blades 31 and the number of sloped surfaces are just exemplarily mentioned, and it should be understood that they are not limited to the examples as shown in the figures.

Each cutting blade 31 has a side surface at which a guide 33 of a predetermined thickness is provided, thereby preventing the drill from being shaken during a drilling work. As shown in FIG. 1, each guide 33 extends in a lengthwise direction of the drill. Also, the guides 33 are approximately configured to be shaped as a circle when they are connected to each other, as shown in a plane view of FIG. 2.

In addition, as shown in FIGS. 1 and 3, a leading edge portion 32 of the cutting blade 31 preferably has a shape curved toward a leading direction as it goes to a distal end of the cutting blade 31 in order to improve the cutting performance of the drill and to easily discharge bone chips. Accordingly, the leading edge portion 32 has an approximately gradual hook shape.

A chip pocket 35 is preferably formed between the cutting blades 31 so that cut bone chips may be easily discharged therethrough as well as temporally stored therein.

On an outer circumference of the body between the connection portion 20 and the cutting portion 30, a stepped portion 11 protruding outwards and a stop portion 12 further protruding outwards from a proximal end of the stepped portion 11 may be formed. The stepped portion 11 and the stop portion 12 may be inserted into and fixed with a stopper member 40 as shown in FIG. 5. The stepped portion 11 may be sized so that it may be fitted into the stopper member 40, and the stop portion 12 prevents further insertion of the stopper member 40. The stopper member 40 may allow a drilling depth to be restricted, which further facilitates the surgery of an operator.

Hereinafter, the operations of the drill as configured above according to the illustrated embodiment of the present invention will be explained with reference to FIG. 6.

As shown in FIG. 6, in case a drilling work is performed using the drill according to embodiments of the present invention, some crumbled bone fragments (i.e., bone chips) may be easily discharged through the chip pocket 35 and stored in the chip pocket 35 while a bone B continues to be cut. At the same time, the mucous membrane M in the maxillary sinus may be lifted while some bone chips generated around the rounded portion of the outer circumferential edge of the drill tip of the drill and the first and second sloped surfaces 31*a* and 31*b* are discharged toward the bone disk D of a conical shape (i.e., through a space between the bone disk D and the first and second sloped surfaces 31*a* and 31*b* of the cutting portion 30). As shown in FIG. 6, the mucous membrane M in the maxillary sinus is lifted in a direction vertical to an inner surface of the maxillary sinus, and at the same time some horizontal regions of the mucous membrane horizontal to the inner surface (in other words, some regions around a hole formed by the drill) may also be lifted.

In addition, since the drill tip of the cutting portion 30 of the drill according to embodiments of the present invention is shaped as the reverse conical shape as explained above, the bone disk D of cancellous bone or cortical bone having the approximately conical shape remains at the front of the cutting portion 30 at the instant that the bone B such as the maxillary sinus is perforated. Due to this bone disk D, the mucous membrane M, such as a mucous membrane in the maxillary sinus, may be safely lifted.

The drill for the implant surgery according to one particularly advantageous embodiment of the present invention has been described with reference to the exemplarily drawings, but the present invention is not limited to the embodiments described above and the accompanying drawings, but it will be apparent that those skilled in the art might make various modifications and changes thereto within the scope of the invention defined by the claims.

Moreover, the various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A drill for use in an implant surgery, the drill comprising:
   a connection portion formed at an upper end of a body of the drill to be connected with a driving device; and
   a cutting portion formed at a lower end of the body and having a plurality of cutting blades for drilling,
   wherein an outer circumferential portion of a distal end of the cutting portion protrudes in a rounded, convex dome shape relative to a center of the distal end of the cutting portion that is concavely depressed and is configured such that a bone disk is formed at the distal end of the cutting portion during a drilling work, and such that a mucous membrane is prevented from being damaged even though the cutting portion is in direct contact with the mucous membrane during the drilling work,
   wherein each of the plurality of cutting blades includes a guide portion that extends parallel to a longitudinal axis of the drill and a leading cutting face that extends from a distal end of the guide portion and is defined in part by a leading edge that is curved radially inward toward a central axis of the cutting portion and curved toward a cutting direction of the drill as the leading edge extends to a distal end of the cutting blade, the leading cutting face of the cutting blade having a hook shape that is curved toward the cutting direction of the drill as the leading cutting face extends to the distal end of the cutting blade, and
   wherein a respective chip pocket is formed between adjacent cutting blades of the plurality of cutting blades so that cut bone chips are easily discharged therethrough and stored therein, one face of the chip pocket being defined by the leading cutting face from one of the adjacent cutting blades, which has the hook shape that is curved toward the cutting direction of the drill, and another face of the chip pocket being defined by a trailing face of the other one of the adjacent cutting blades, the trailing face being a flat surface parallel to the longitudinal axis of the drill.

2. The drill as claimed in claim 1, wherein each of the cutting blades has one or more sloped surfaces at an inner side of a tip thereof.

3. The drill as claimed in claim 2, wherein the guide portion of each cutting blade has a predetermined thickness at a side surface thereof, thereby preventing the drill from being shaken during the drilling work.

4. The drill as claimed in claim 1, wherein a stepped portion protruding outwards from the body and a stop portion further protruding outwards from a proximal end of the stepped portion are formed on an outer circumference of the body between the connection portion and the cutting portion, whereby a stopper member for restricting a drilling depth may be fixedly fit around the stepped portion.

5. A drill for use in an implant surgery, the drill comprising:
- a cutting portion having a plurality of cutting blades for drilling, each cutting blade having a distal shape with a sloped surface configured so that a bone disk is formed and a mucous membrane in a maxillary sinus may be lifted while some bone chips generated during a drilling work are discharged through a space between the sloped surface and the bone disk,
- wherein each cutting blade includes a guide portion that extends parallel to a longitudinal axis of the drill and a leading cutting face that extends from a distal end of the guide portion and is defined in part by a leading edge that is curved radially inward toward a central axis of the cutting portion and curved toward a cutting direction of the drill as the leading edge extends to a distal end of the cutting blade, the leading cutting face of the cutting blade having a hook shape that is curved toward the cutting direction of the drill as the leading cutting face extends to the distal end of the cutting blade,
- wherein an outer circumferential portion of a distal end of the drill is rounded to define a convex profile at the outer circumferential portion, and
- wherein a respective chip pocket is formed between adjacent cutting blades of the plurality of cutting blades so that cut bone chips are easily discharged therethrough and stored therein, one face of the chip pocket being defined by the leading cutting face from one of the adjacent cutting blades, which has the hook shape that is curved toward the cutting direction of the drill, and another face of the chip pocket being defined by a trailing face of the other one of the adjacent cutting blades, the trailing face being a flat surface parallel to the longitudinal axis of the drill.

* * * * *